United States Patent
Sundrehagen

(10) Patent No.: US 6,716,641 B1
(45) Date of Patent: Apr. 6, 2004

(54) DIPSTICK FOR CARBOHYDRATE-FREE TRANSFERRIN ASSAY

(75) Inventor: Erling Sundrehagen, Oslo (NO)

(73) Assignee: Axis-Shield ASA, Oslo (NO)

(*) Notice: Subject to any disclaimer, the term of this patent is extended or adjusted under 35 U.S.C. 154(b) by 0 days.

(21) Appl. No.: 09/856,484

(22) PCT Filed: Dec. 10, 1999

(86) PCT No.: PCT/GB99/04191

§ 371 (c)(1),
(2), (4) Date: Sep. 14, 2001

(87) PCT Pub. No.: WO00/36418

PCT Pub. Date: Jun. 22, 2000

(30) Foreign Application Priority Data

Dec. 11, 1998 (GB) .............................. 9827411

(51) Int. Cl.⁷ .............................. G01N 33/53
(52) U.S. Cl. .................. 436/514; 435/7.1; 435/287.1; 435/287.2; 435/810; 435/962; 435/973; 435/975; 436/161; 436/177; 436/178; 436/512; 436/518; 436/524; 436/528; 436/529; 436/531; 436/534; 436/808
(58) Field of Search .............................. 435/7.1, 287.1, 435/287.2, 810, 962, 973, 975; 436/161, 177, 178, 512, 514, 518, 524, 528, 529, 531, 534, 808

(56) References Cited

U.S. PATENT DOCUMENTS

| | | | |
|---|---|---|---|
| 4,435,504 A | 3/1984 | Zuk et al. .......................... 435/7 |
| 4,626,355 A | 12/1986 | Joustra et al. | |
| 4,703,017 A | 10/1987 | Campbell et al. ........... 436/501 |
| 4,855,240 A | 8/1989 | Rosenstein et al. ......... 436/514 |
| 5,075,078 A | 12/1991 | Osikowicz et al. ........... 422/56 |
| 5,290,678 A | 3/1994 | Jackowski .................. 435/7.4 |
| 5,591,645 A | 1/1997 | Rosenstein .................. 436/514 |
| 5,658,801 A | 8/1997 | Poissant et al. ............. 436/518 |
| 5,766,552 A * | 6/1998 | Doshi et al. | |

FOREIGN PATENT DOCUMENTS

| | | |
|---|---|---|
| WO | 91 19983 A | 12/1991 |
| WO | 94/15215 | 7/1994 |
| WO | 95 04932 A | 2/1995 |
| WO | 96 22532 A | 7/1996 |
| WO | 96 26444 A | 8/1996 |
| WO | 97/19355 | 5/1997 |
| WO | 98/32004 | 7/1998 |
| WO | 98 54576 A | 12/1998 |
| WO | 99 00672 A | 1/1999 |
| WO | 99 60402 A | 11/1999 |

OTHER PUBLICATIONS

Wong and Regoeczi, "Some Observations on the Carbohydrate Composition of Purified Transferrin", Int. J. Peptide Protein Res. (1977) 9:241–248.

(List continued on next page.)

Primary Examiner—Bao-Thuy L. Nguyen
(74) Attorney, Agent, or Firm—Bacon & Thomas, PLLC

(57) ABSTRACT

The invention relates to a new dipstick assay for detecting and quantifying the content of an target analyte in a sample. The assay is particularly useful for example in the diagnosis and monitoring of alcoholism by the detection of asialo transferrin or carbohydrate free transferrin (CFT). Thus, provided is a dipstick for determining the content of a target analyte variant in a mixture of analyte variants in a sample, comprising: a) a sample application zone, b) a screening zone having an immobilised binding ligand having a binding affinity for a non-target analyte variant or varinats, c) a conjugate zone comprising a detector reagent, d) a reading zone for detection of said analyte.

14 Claims, 1 Drawing Sheet

Figure 1:
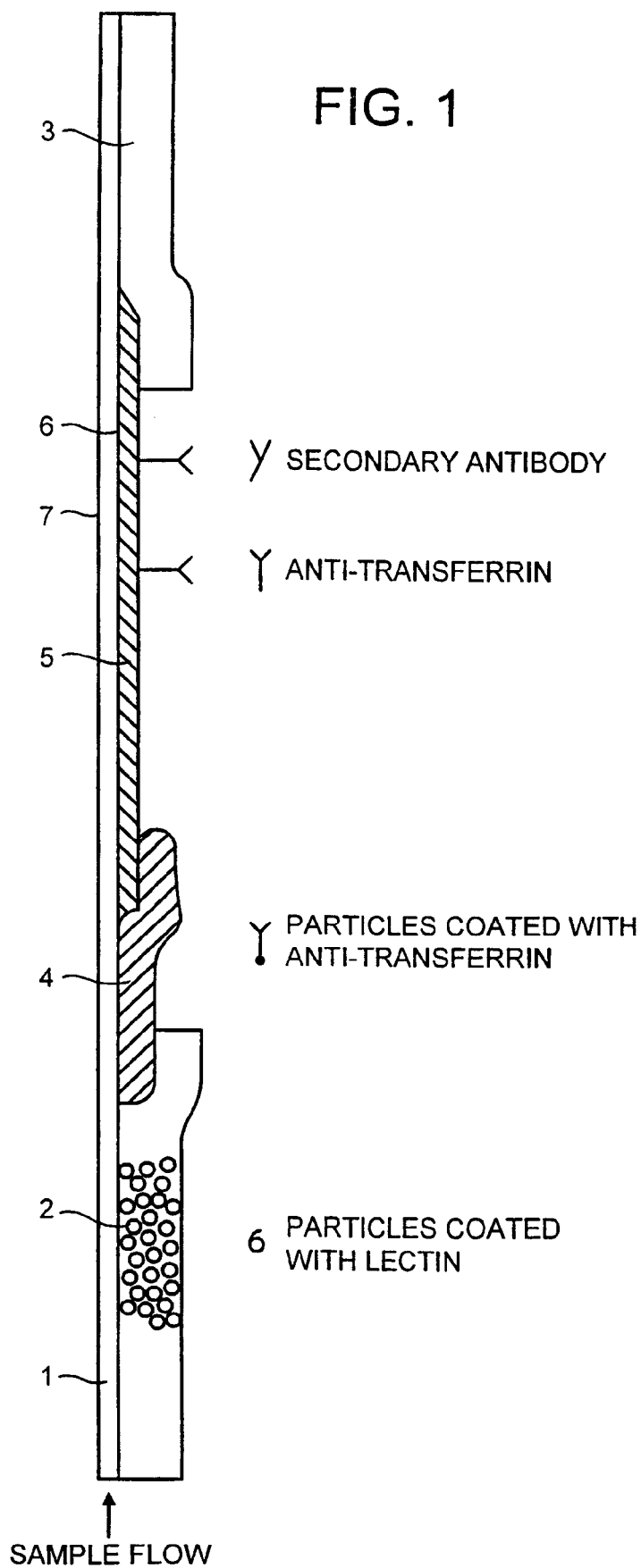

OTHER PUBLICATIONS van Eijk et al., "The microheterogeneity of human transferrins in biological fluids", (1983) Clin Chim Acta 132:167–171.

Stible, "Carbohydrate–Deficient Transferrin in Serum: a New Marker of Potentially Harmful Alcohol Consumption Reviewed", (1991) Chin Chem 37/12, 2029–2037.

Stible et al., "Carbohydrate–deficient transferrin (CDT) in serum as a marker of high alcohol consumption", Advances in the Biosciences, Pergamon Press plc, 1988, vol. 71, pp. 353–357.

Heil et al., "Del Stellenwert des kohlenhydratefizienten Transferrin (CDT)", (1994) Anaesthesist 43:447–453.

Dumon et al., "Isoelectric Focusing (IEF) and Immunofixation for Determination of Disalotransferrin" (Dec. 1996) Clin. Biochem. 29(6):549–553.

Landberg et al., "Carbohydrate Composition of Serum Transferrin Isoforms from Patients with High Alcohol Consumption", (May 16, 1995) Biochem. Biophys. Res. Comm. 210(2):267–274.

Ajit Varki, "Selectins and other mammalian sialic acid–binding lectins", (1992) Current Opinion in Cell Biology 4:257–266.

Kornfeld et al., "The Carbohydrate–binding Specificity of Pea and Lentil Lectins", (Jan. 23, 1981) J. Biol. Chem. 256:13, pp. 6633–6640.

Ersson, "A Phytohemagglutinin from Sunn Hemp Seeds (*Crotalaria Juncea*)", (Apr. 4, 1977) Biochim. Biophys. Acta 494:51–60.

Mandal and Manda, "Sialic Acid Binding Lectins", (1990) Experientia 46:433–441.

Shibuya et al., "The Elderberry (*Sambucus nigra L.*) Bark Lectin Recognizes the Neu5Ac($\alpha$2–6)Gal/GalNAc Sequence", (Feb. 5, 1987), J. Biol. Chem. 262:1596–1601.

Lelwala–Guruge et al., "Rapid detection and characterization of sialic acid–specific lectins of *Helicobacter pylori*", (Feb. 25, 1993), APMIS 101:695–702.

Fu–Yue Zeng, "Sialic Acid–Binding Proteins: Characterization, Biological Function and Application", (May 11, 1992) Z. Naturforschung, 47c:641–653.

Reuter and Schauer, "Determination of Sialic Acids", (1994) Methods in Enzymology, vol. 230, Chapter 10, pp. 196–198.

Martensson et al., "Transferrin Isoform Distribution: Gender and Alcohol Consumption", Alcoholism: Clinical and Experiemntal Research, vol. 21, No. 9 p 1710–1715, Aug. 5, 1997.

\* cited by examiner

DIPSTICK FOR CARBOHYDRATE-FREE TRANSFERRIN ASSAY

The present invention relates to a new dipstick assay for detecting and quantifying the content of an analyte in a sample. The assay is particularly useful for example in the diagnosis and monitoring of alcoholism by the detection of asialo transferrin or carbohydrate free transferrin (CFT).

Many biological proteins exist in two or more variant forms, frequently differing in the extent of glycosylation of the protein or in the carbohydrate composition per se. Other forms of variation may be in the lipid content or composition of the molecule, or even differences in the primary, secondary or tertiary structures of the protein. The relative concentrations of such variants in a given body tissue or fluid are generally constant, but may be disturbed in certain diseases or pathological states, or as a result of other disturbances to the body. The ratio, for example, of glycosylated to non-glycosylated haemoglobins is known to increase in the serum of patents suffering from diabetes. Similarly, some structural proteins for example, myoglobins, may have slight structural differences in different organs and may be released into the bloodstream following cell damage resulting from disease or injury.

Thus, by measuring the levels of the different variants of a protein in the blood or body fluid of interest, a diagnosis or assessment of a disease or cellular damage can be made.

Serum transferrin is a glycoprotein with a molecular weight of about 80 kD which comprises a single polypeptide chain with two N-linked polysaccharide chains. These polysaccharide chains are branched and each chain may terminate in either two or three antennae, each with terminal sialic acid residues.

Wong and Regoeczi, in Int. J. Peptide Res. (1977) 9:241–248, reported that human transferrin was naturally heterogeneous, occurring in variant forms with different levels of sialylation. Until recently, there were generally believed to be six such variants, the pentasialo, tetrasialo, trisialo, disialo, monosialo and asialo transferring. Many researchers working in the field of chromatographic analysis of transferrins have however reported that the levels of monosialo transferrin are very low.

The asialo, monosialo, disialo and trisialo variants are often referred to collectively within the field as carbohydrate-deficient transferrin or CDT.

In the normal healthy individual, the tetrasialo variant appears to predominate; however it has been reported that the asialo, monosialo, disialo and, to some degree the trisialo variants, ie. CDT, occur in elevated levels in the blood of alcoholics (see van Eijk et al. (1983) Clin Chim Acta 132:167–171, Stibler (1991)Chin Chim 37:2029–2037 and Stibler et al. in "Carbohydrate-deficient transferrin (CDT) in serum as a marker of high alcohol consumption", Advances in the Biosciences, (Ed Nordmann et al), Pergamon, 1988, Vol. 71, pages 353–357).

CDT has been shown to be an effective marker for—alcohol consumption, in particular for detecting and monitoring chronic alcohol consumption. Monitoring of blood alcohol level is reliable only when blood is sampled within 24 hours of alcohol consumption and conventional tests (for example, quantitation of γ-glutamyltransferase or measurement of mean corpuscular volume) cannot reliably be used to screen for heavy alcohol intake in patients with liver disease.

Early investigations showed that loss of the sialic acid residues correlated with changes in the isoelectric point (pI) of the transferrin molecules, for example, asialotransferrin exhibits a pI of 5.9, disialotransferrin exhibits a pI of 5.7 and so on. Recognition of the fact that the CDT profile of alcohol abusers differs from that of abstainers or normal users, combined with the identification of the relative amounts of each CDT isoform on the basis of pI, has led to the development of several diagnostic assays for CDT which are described in the patent and scientific literature.

A chromatography assay using anionic ion exchange of the sample to allow asialo, monosialo and disialo CDTs to be eluted whilst the "normal" tetra and pentasialo variants are retained on the column, is disclosed in U.S. Pat. No. 4,626,355 (Joustra) of Pharmacia AB.

An assay using isoelectric focussing and immuno-fixation techniques has been proposed in Dumon et al., (1996) Clin. Biochem. 29(6): 549–553 to assess disialotransferrin content of a sample.

However, these prior art methods for CDT analysis rely on differences in the pI or charge of the different transferrin isomers. Such methods tend to rely upon relatively complex procedures.

Traditionally, it has been thought that CDT arises from a loss of the terminal sialic acid residues of the carbohydrate side chains and it is upon this that the various prior art pi or charge based assays have been predicated (namely, that a loss of a charged sugar moiety would alter the charge and pH of the isoform as a whole).

However, recent studies (for example by Landberg et al. (1995) Biochem. Biophys. Res. Comm. 210(2): 267–274), have shown, by releasing the N-glycans from each isoform of transferrin and analysing them by high-pH anion exchange chromatography, that contrary to this understanding, the existence of disialo and asialo-transferrins appears rather to be correlated with the loss of one or both of the entire carbohydrate chains respectively from the transferrin polypeptide. This "deglycosylation" is not yet fully understood.

The carbohydrate chains may be bi or triantennary and hence each carbohydrate chain in its normal state will carry two or three sialic acid residues, one at the terminus of each antenna. It may be that the carbohydrate chains are cleaved from the transferrin molecules at their base in a single step process, i.e. at an asparagine molecule in the amino-acid backbone of the protein, leaving no sugar residues at that particular glycosylation site. Alternatively, individual or multiple sugar residues may be sequentially lost from transferrin molecules resulting in a gradual loss of carbohydrate content. It is also possible that the CDT transferrin molecules are never properly glycosylated in the first place due to aberrant enzymatic glycosylation processes.

To date, the prior art has favoured the idea that either measurement of all of the CDT variants ie. asialo, monosialo, disialo and trisialo transferrin, or at least two or more CDT variants was necessary to make a meaningful clinical evaluation, or that measurement of the disialotransferrin on its own was necessary.

Contrary to this trend in the art, the Applicants developed and described in WO99/00672 a new type of assay for detecting carbohydrate free transferrins (CFTS). This assay is based on the principle that the presence of transferrin isoforms which are completely devoid of carbohydrate, ie. carbohydrate free transferrin (CFT), is a strong indicator of alcoholism in the absence of any knowledge of the prevalence of any other CDT variants (ie. monosialo, disialo or trisialotransferrin variants). The assay is robust, simple and quick to perform, and readily amenable to automation or compatible with existing routine clinical diagnostic laboratory procedures. This is achieved by separating the carbohydrate-containing transferrins from a sample by contacting them with a carbohydrate-binding ligand and detecting and measuring the carbohydrate-free transferrin contained in the separated, non-binding fraction. However, it was not previously proposed to produce this assay in the form of a dipstick.

Dipsticks represent a solid phase format in common usage in the diagnostic field and indeed form the basis of many home testing kits e.g. home pregnancy testing kits. Many types of dipstick assay have been proposed in the prior art and many of these rely on the principles of the binding affinity of an analyte for a particular binding partner. Many different combinations of analyte:binding partner have been successfully employed in dipstick assays, and many different techniques have been devised which allow visible results to be obtained.

For example, WO 94/15215 of Medix Biochemica discloses a test strip for analysing environmental pollutants, and uses a mobile labelling reagent which contacts an immobilised test zone in a void space between a test membrane and a backing strip which forms a reaction chamber. This assay is suitable for a wide variety of analytes including biological compounds for the diagnosis of physiological conditions in humans.

U.S. Pat. No. 4,435,504 discloses a dipstick assay which allows quantification of the analyte content of a sample in which the analyte saturates the immobilised binder on the dipstick at a given distance from the point of sample application and this gives a measurement of analyte content.

U.S. Pat. No. 5,075,078 of Abbott Laboratories discloses an improved dipstick assay allowing visualisation of positive and negative results by specific orientation of the immobilised control zone in a + and − format.

U.S. Pat. No. 5,290,678 and U.S. Pat. No. 5,658,801 of Spectral Diagnostics Inc. disclose diagnostic test kits for diagnosing myocardial infarction using polyclonal or monoclonal antibodies to test for specific proteins in blood or serum samples.

None of the dipstick assays used or proposed in the prior art are suitable for detecting the presence of CFT's in order to enable a diagnosis of alcoholism or alcohol abuse to be made, or indeed to detect selectively any desired variant or subset of variants of an analyte. These dipstick assays are suitable for a wide variety of analytes, but they rely on the use of a specific binding partner for the analyte, which can make it difficult to obtain meaningful results where the samples under analysis are likely to contain variants of the analyte, and it is desired to detect only one or a subset of the variants.

According to the present invention, a novel form of dipstick assay has now been developed that is surprisingly and particularly suitable for obtaining meaningful results in such circumstances. For example, the dipstick assay of the present invention finds particular utility in detecting and quantifying any analyte which is naturally present in the body in a number of variant forms, particularly variant forms having carbohydrate-containing and carbohydrate-free variants. The dipstick assay of the present invention allows different variant forms of such an analyte to be discriminated.

In one aspect, the present invention accordingly provides a dipstick for determining the content of an analyte variant (a "target analyte variant") in a mixture of analyte variants in a sample, comprising:

a) a sample application zone;
b) a "screening zone" having an immobilised binding ligand having a binding affinity for a variant(s) of said analyte which is (are) not to be determined (ie. non-target analyte variant(s));
c) a conjugate zone comprising a detector reagent;
d) a reading zone for detection of said analyte.

The dipstick of the present invention is particularly suitable to detect transferrin isoforms which are completely devoid of carbohydrate, i.e. carbohydrate-free transferrin (CFT).

A further advantage of the dipstick assay format is that it involves a quick and convenient one-step procedure which may be carried out anywhere and at any time. There is no need for special training in order to carry out the test using a dipstick assay, as the results are obtained in a short space of time and are readily interpreted by means of a visible result on the dipstick. No special reagents are needed to carry out the test, as all the necessary reagents and detection material are contained within the dipstick.

Thus, diagnosis and assessment may conveniently be carried out during a visit to a general practitioner's clinic or even during a home visit to a patient, and could be undertaken by a nurse or doctor without the need to use expensive laboratory equipment or send away samples for analysis by an outside laboratory.

By the term "dipstick" is meant any device which is capable of being dipped into a sample or having a sample applied thereto and which allows the sample to diffuse or be transported along one or more of its dimensions. This includes any of the known dipstick formats suitable for testing and analysing biological samples which would be familiar to a person skilled in the art, but is not limited thereto. Thus, the "dipstick" of the invention is in other words a solid support test device. The traditional "dipstick" configuration known in the art is convenient, but the invention encompasses all solid support test device configurations which are known in the art. Advantageously, the zones are arranged on the dipstick in the same plane in a manner such that the material (e.g. sample fluid and/or reagents) can flow from the first to the subsequent zones, preferably sequentially from zone to zone. Although the preferred shape is in the form of a strip, any other of a wide variety of shapes or forms may be employed as long as the shape and form permits separate zones for performing the various functions, as described herein. Advantageously, the configuration of the dipstick is such that the direction of flow is generally parallel to the length of the dipstick. The dipstick of the invention may thus be regarded as being akin to the immunochromatography test strips which are known in the art, but, as will be explained in more detail below, is not limited to the use of "immuno" reagents ie. antibodies. Dipstick structures, builds or configuration according to the invention may be any of those standard in the art and described in the literature, including the patent applications listed above.

The term "determining the content" includes both quantitation in the sense of obtaining an absolute valve for the amount of the target analyte variant(s) in the sample, and also semi-quantitative and qualitative assessments or determinations. An index, ratio, percentage or any other indication of the level or amount, or indeed the presence or absence, of a target variant, may be obtained, for example relative to the total analyte variant population (ie. all analyte variants). Visual readout formats (assessments or determinations) are particularly included.

The analyte to be determined may be any analyte of clinical or diagnostic relevance e.g. any biomolecule, which occurs in variant forms (e.g. isoforms). Preferably however it will be a protein, and more preferably a protein having variant forms which differ in carbohydrate content and/or composition. Whilst analytes of clinical relevance are preferred, that is analytes occurring in the body, other analytes, e.g. those of environmental or forensic significance are also included, for example analytes relevant to contamination testing e.g. of food or water.

The dipstick of the invention has particular utility in the detection or measurement of target analyte variants which either do not contain carbohydrate e.g. CFT (or asialotransferrin which is now believed by some parties to be devoid of all carbohydrate and not just sialic acid groups) or which have an altered carbohydrate content, as compared with the non-target variants of the analyte in question. Particular mention may be made of asialo compounds, for example asialo-transferrin, asialo-orosomucoid, asialo-fetuin or asialo-ceruloplasmin.

The target analyte variant ie. the analyte variant to be determined may thus be a single variant e.g. a protein variant completely free of carbohydrate such as CFT, or asialotransferrin (whether this is viewed as being completely free of carbohydrate, or simply as having lost all sialo groups) or a group or subset of variants (e.g. transferrin variants which have lost-sialo groups but which may retain residual oligosaccharide chains of variable composition). As will be described in more detail below, the target variants may also comprise variants of CDT e.g. mono- and asialo-transferrins, or di-, mono- and asialo-transferrins. Thus the term "analyte variant" includes one or more than one variant species.

The sample may be any analyte-containing sample it is desired to assay, but preferably it will be a body fluid including synovial fluid, amniotic fluid or cerebrospinal fluid, but will generally be blood or a blood-derived sample, or urine. The sample may however be any clinical or environmental sample, and may include clinical samples where any body tissue or cells are disrupted or otherwise prepared in a fluid or suspension form. In particular, the sample may be any transferrin-, orosomucoid-, fetuin- or ceruloplasmin-containing body sample. Where a blood-derived sample is used, the sample for analysis will preferably be cell-free, and hence will be either serum or plasma may be used. The sample may be treated prior to being applied to the dipstick for determination of the analyte, for example it may be diluted by adding buffer or any other suitable aqueous medium.

The sample application zone allows sample to enter the dipstick, and may be of any format and made from any material which allows this. The sample application zone is preferably made from glass fiber, cellulosics, other polymers woven fibers or non-woven filters but may be made from any other suitable material which, where necessary, serves to retard penetration of the sample, distribute the sample and remove any particulates which may be present in the sample. The technology for this is standard and well known in the art. The sample application zone may also conveniently comprise or contain means for determining the volume of sample which flows further into the dipstick. This is discussed in more detail below.

The "screening zone" having an immobilised binding ligand is preferably located in close proximity to the sample application zone and is in contact either directly or indirectly with said sample application zone such that the sample may flow into said screening zone and through said screening zone prior to entering the conjugate zone. Conveniently, the screening zone is arranged to be in capillary flow communication with the sample application zone. Methods and means of achieving such functional requirements are a common feature of dipstick technology and are known in the art. In an alternative preferred embodiment, the screening zone may form an integral part of the sample application zone, e.g. the immobilised binding ligand in feature (b) of the dipstick may be contained within the sample application zone, or the same zone may function both as sample application and screening zone. In other words the screening zone and the sample application zone may be one and the same zone.

Conveniently, the screening zone and the sample application zones are in the form of one or more pads, the screening zone having the binding ligand immobilised thereon or therein. Again such "pads" are part of well known dipstick technology and will be described in more detail below. Where more than one pad is used, it is important that consecutive pads should be in functional contact with one another in order to allow free flow of the sample through the dipstick. Where the sample application zone and the screening zone coexist together as an integral part of the dipstick, the screening zone and the sample application zone may take the form of a single pad or a multiplicity of pads, each of which are suitable for application of the sample and screening of the variant of the analyte under test.

The purpose of the screening zone is to remove from the sample, and hence from being detected, those variant of the analyte it is not desired to detect. In other words the screening zone "screens out" the non-target variants, allowing only the target variants to pass through to detection (ie. to contact the conjugate zone). Thus, this feature of the invention allows the target and non-target variants of the analyte to be discriminated. By using a binding ligand having a binding affinity for non-target variant(s) of said analyte, the target analyte is able to pass through the screening zone whereas the non-target variants of said analyte are retained within the screening zone by binding to the immobilised binding ligand.

The binding ligand which is immobilised in or on the screening zone is any ligand capable of binding selectively to the non-target variant(s) it is not desired to detect. The term "binding affinity" is thus used herein simply to mean that the binding ligand reagent in question is capable of binding to the binding partner specified.

Thus, for example, in the case of non-target variants which differ from the target variants in the presence of a particular moiety e.g. a carbohydrate or a lipid or some other group e.g. a prosthetic group, then the binding ligand may be any ligand capable of binding selectively to that group, but not to the target variant.

Preferably, the immobilised binding ligand of the "screening zone" is a compound which is able to bind carbohydrate-containing moieties, such as a lectin or a mixture of lectins. Particularly suitable binding ligands would be for example SNA lectin, Con A lectin and mixtures thereof, these being binding partners for carbohydrate-containing transferring.

Any binding ligand which has an affinity for a variant of the analyte contained in the sample or any combination thereof may thus be used to separate the target analyte from other variants of the analyte. Where the target analyte variant is a carbohydrate-free protein with carbohydrate-containing variant(s) being separated from it, the binding ligand will be a carbohydrate-binding ligand. This includes any ligand capable of binding to any carbohydrate or oligosaccharide or sugar structures. One or more carbohydrate-binding ligands may be used in the dipstick assay of the invention. Generally, the carbohydrate-binding ligand will be a protein, and very many such carbohydrate-binding proteins are known in the art and are widely described in the literature. The carbohydrate-binding protein may, for example, be an antibody, either polyclonal or monoclonal, or may be an antibody fragment for example F(ab), F(ab')$_2$ or F(v) fragments. The antibodies or antibody fragments may be monovalent or divalent and they may be produced by hybridoma technology or be of synthetic origin, via recombinant DNA technology or chemical synthesis. Single chain antibodies could for example be used. The antibody may be directed or raised against any of the carbohydrate components or structures making up the carbohydrate chains of glycosylated analyte (e.g. transferrin) variants. Thus, for example, an antibody reactive with or selective for sialic acid residues might be used. Such an antibody is used in the Sialic Acid Deficient Enzyme Immunoassay (SDT-EIA) available from Medichem, Stuttgart., Germany and described in WO97/19355.

More preferably, the carbohydrate-binding protein may be a lectin, used singularly or in combination with other lectins or with other types of carbohydrate-binding proteins, for example, antibodies. Any lectin known in the art may be used in the dipstick assay of the invention and it may be of plant, animal, microbiological or any other origin. The literature is replete with references to different lectins which might be used, and many may be obtained commercially, for example, from Sigma.

Thus, included within the general term "lectin" as used herein, in addition to the classical plant lectins such as Concanavalin A (Con A), are carbohydrate binding proteins from microorganisms (for example, viral haemagglutinins) and higher organisms, including for example, invertebrates and mammals. Such mammalian carbohydrate binding proteins include selectins and other mammalian lectins or cell adhesion molecules (see for example Varki (1992) Current Opinion in Cell Biology 4:257–266).

Where CFT or another carbohydrate free protein is the desired target variant, a functional requirement of the carbohydrate binding ligands, rendering them suitable for use in the dipstick assay of the present invention, is that they be capable of separating carbohydrate-free variants e.g. CFT from other analyte carbohydrate-carrying variants (e.g. transferrin variants) bearing one or more oligosaccharide chains, in an entire or degraded form.

Whilst a single type of binding ligand may be used according to the invention, conveniently more than one such binding ligand may be used and even more conveniently, a number of different carbohydrate binding ligands may be used. Where the binding ligand is a carbohydrate-binding ligand, each may have a different sugar or oligosaccharide binding capacity. Thus, in one preferred embodiment, a panel of different binding ligands with differing selectivity and specificity is used.

Where more than one ligand is being used, these may be immobilised in the screening zone either in random mixed fashion on the dipstick support, or the screening zone may consist of one or more distinct, separate areas each containing a different immobilised ligand. Thus, for example, the screening zone may comprise more than one pad having one or more different binding ligands immobilised thereon. Provided that the screening zone is able to fulfill its function of achieving separation of the non-binding analyte (ie. the target variant) from the variants of the analyte which do bind to the binding ligand prior to contact of the sample with the conjugate zone, the sequence of the binding ligands contacted by the sample may be in any sequential order or it may involve simultaneous contact with all the different ligands.

Combinations of different ligands are preferred due to the increased binding capacity which may be provided by two or more ligands and hence better separation of the transferrin isoforms. Many carbohydrate binding ligands for example, lectins, have low binding affinities for their sugar or oligosaccharide binding partners and the synergistic binding capacity provided by more than one ligand is advantageous.

Examples of suitable lectins are RCA-I (Ricinus communis agglutinin) which binds terminal galactose (Kornfeld et al. (1981) J. Biol. Chem. 256:6633) or Con-A (Concanavalin A), which is known to bind asparagine-linked oligosaccharides high in mannose. Other possibilities are Crotalaria juncea lectin which binds galactose residues (Ersson (1977) Biochim. Biophys. Acta 494:51–60), Wheatgerm agglutinin or Limulus polyphenus lectin which bind sialic acid (Mandal and Mandal(1990) Experientia 46:433441) or *Sambucus nigra* agglutinin L (SNA) which binds Neu5Ac/($\propto$2–6)Gal/GalNAc (Shibuya et al. (1987) J. Biol. Chem. 262:1596). As an example of a lectin derived from a micro-organism, a sialic acid specific lectin has recently been purified from the gut dwelling organism *Helicobacter pylori* (Lelwala-Guruge et al. (1993) APMIS 101:695–702).

Lectins of varying selectivity and specificity are known. Whereas some lectins may bind to a single sugar residue in a particular location on an oligosaccharide chain, for example RCA-I (from *Ricinus communis*) binds only to terminal galactose residues, some may bind to complex oligosaccharide determinants for example *Sambucus nigra* L which binds Neu5Ac/($\propto$2–6)Gal/GalNAc. All are within the scope of the present invention.

Sialic acid binding lectins and other proteins represent a class of carbohydrate binding proteins of particular utility in the present invention (see the following, for example, for lists of suitable lectins and their sources: Mandal and Mandal(1990) Experientia 46:433–441); Zeng (1992) Z. Naturforsch, 47c:641–653 and Reuter and Schauer in Methods in Enzymology, Vol. 230, Chapter 10 at pages 196–198).

Particular mention may be made in this regard of Sambucus nigra L. Lectin (SNA), *Sambucus sielbodiana* lectin wheatgerm agglutinin, *Maackia amurensis* lectin, and *E. coli* K99 lectin. SNA is particularly effective when used on its own, although it may equally effectively be used in combination with other lectins eg. ConA. Combinations of ConA with SNA are preferred.

Some particular combinations of carbohydrate binding ligands useful for performance of the present invention are lectins from *Helicobacter pylori* and *Ricinus communis*; lectins from *Ricinus communis* and *Sambuccus nigra*; lectins from *Crotalaria junctae* and *Sambuccus nigra*; lectins from *Crotalaria junctae* and *Helicobacter pylori* and lectins from *Ricinus communis* and anti-sialic acid antibodies. The most preferred of the combinations are those which incorporate galactose-binding and sialic acid-binding ligands.

As mentioned above, the detection of CFT represents a preferred utility according to the present invention and accordingly preferred lectins are those which bind to the mono- and oligosaccharide arrangements of the transferrin carbohydrate side chains with a kD of $10^4$ or greater. Lectins with a lower binding affinity may also be used, but preferably at a higher density.

When the sample comprising the analyte variants is contacted with the binding ligands immobilised in the screening zone, all or substantially all of the variants having a binding affinity for the binding ligand are retained in the screening zone. Thus where CFT is the analyte, all transferrin variants (which may include CDT variants) with carbohydrate side chains or remnants thereof may be retained by the carbohydrate-binding ligands and only the carbohydrate-free transferrin is not bound to the ligands. The unbound, carbohydrate-free transferrin containing fraction (ie. the substantially carbohydrate-free fraction) then continues along the dipstick towards the conjugate zone, leaving the other variants behind in the screening zone.

However, it will be understood that variations of the invention are possible, and with appropriate selection of binding ligands any desired subset of non-target variants may be retained. Thus, for example, lectins or antibodies with affinity for particular carbohydrate groups may be selected to bind to variants containing those groups. In this manner e.g. sialo-containing variants may be retained by binding to sialic acid-specific binding ligands. However variants having no sialo groups, even though they may have other carbohydrate moieties, may be separated. As will be further described below, further preferred subsets of desired target analyte variants include asialo-(CFT) and disialo-transferrins or asialo-, monosialo- and disialo-transferrins.

Thus in the case where the analyte is an asialo protein such as asialotransferrin, this passes through the screening zone without being retained, whereas variants of the analyte such as sialotransferrins (including pentasialo, tetrasialo, trisialo, disialo and monosialo transferring) are retained in the screening zone.

Thus, the invention permits analyte variants to be separated on the basis of carbohydrate composition as well as content, and analogous principles apply to other chemical moieties such as lipids, the content or composition of which may vary between analyte variants.

The binding ligand is immobilised in the screening zone of the dipstick in order to facilitate the separation and subsequent detection and measurement of the non-binding fraction containing the target analyte. It is well known in the art to immobilise a wide variety of binding ligands such as carbohydrate-binding ligands.

The binding ligands may thus be immobilised by binding, or coupling to a solid support. This may be any of the well known solid supports or matrices which are currently widely used or proposed for immobilisation of a ligand. The solid support may thus be a part of the basic dipstick structure itself or it may be a component which is provided in or on the dipstick. Different forms of solid support or matrix may thus include particles, sheets, gels, filters, membranes, fibers or capillaries or microtitre strips etc. For particular use in the form of a dipstick, the support may generally take the form of a sheet, strip, membrane or particles. Advantageously, the support may be, or may comprise a porous material, or a high surface-area material. Conveniently the solid support may be made of glass, silica, latex or a polymeric material, e.g. glass fibre, paper, cellulose and cellulose derivatives such as acetates and nitrates, polyesters, polycarbonates and polyvinyl compounds. Such materials, and their use in dipsticks, are well known in the art. Techniques for binding or coupling of the ligand to the solid support are also extremely well known and widely described in the literature (see for example Immobilised Affinity Ligand Techniques, Ed Hermanson, Mallia and Smith, Academic Press Inc.).

For example, in a preferred embodiment the binding ligand may conveniently be covalently coupled directly to the pads of the screening zone and/or the sample application zone, using any convenient or desired coupling chemistry e.g. a linker, such as cyanogen bromide. Alternatively, and in another preferred embodiment, the binding ligand may be coupled to particles e.g. latex particles. The pad or pads may for example be dipped into a solution containing a ligand-latex conjugate, and then dried. The particles are preferably larger than the pore size of the pad in order to ensure that they are not released from the pad. Other coupling or immobilisation methods for proteins are also well known in the art.

The dipstick of the present invention may take a variety of forms. Dipstick technology is well-known in the art, and in general any form of dipstick which is suitable for the provision of a "screening zone" is preferred. In general, a dipstick will contain a sample application zone in a form which is often known as a "sample pad". This fulfills several functions which aid operation of the dipstick. For example, the sample pad preferably is capable of retarding sample penetration and/or helping to distribute the sample over the conjugate zone. Preferably also it is able to remove particulates from the sample, adjust the pH or viscosity of the sample solution, facilitate the release of the detector reagent, and separate plasma or serum from whole blood. Thus, the sample pad effectively prepares the sample for analysis in the rest of the dipstick.

Sample pads may commonly be made of a variety of materials such as glass fibre filter, cellulosics (paper), woven fibres (meshes) or non-woven filters. Glass fibre filters are available in a wide range of product varieties, are very wettable, have moderately low protein binding characteristics, may have a moderate to high bed volume but have a low tensile strength, especially when wet. Cellulosics (paper) are also available in a wide range of product varieties, are very wettable, have very low protein binding characteristics, may have a moderate to high bed volume but have a very low tensile strength, especially when wet.

Woven fibres (meshes) are available in a more limited range of product varieties, are very wettable, have very low protein binding characteristics and very low bed volume, but have the advantage of a high tensile strength, even when wet. Non-woven filters also have a high tensile strength, even when wet, are available in a wide range of product varieties, but are not intrinsically wettable and have moderate protein binding characteristics. The sample application zone, as mentioned above, also may conveniently contain volume-determining means. Again, technology for this is standard. This may take the form, for example, of a sample pad having a predetermined size and/or void volume. Such a pad may optionally be provided with temporary liquid barrier, which allows the sample pad to be saturated before the liquid dissolves the barrier and the sample is able to flow further into the dipstick. Examples of suitable barriers include dried carbohydrates, proteins, nucleic acids, and organic or inorganic salts.

The conjugate zone (c) to which the sample flows after having been "screened" through zone (b) may be regarded as the zone which functions to provide a means whereby the target analyte variants may subsequently be detected. This zone is thus, as for previous (and subsequent) zones, in flow-communication with preceding zone(s), e.g. capillary flow communication. Thus, a detector reagent is provided to serve this function. The detector reagent interacts with the target analyte, and provides or carries a detectable moiety for subsequent detection in the reading zone. The detectable means or moiety with which the detector reagent is provided or which it carries is conveniently a signal-producing moiety. Thus the detector reagent may comprise or may be conjugated to a signal-giving substance.

The detector reagent may thus be regarded as equivalent to the "tracer" reagents which are known in dipstick/test strip assays conventional in the prior art.

The detector reagent may take different forms depending on the assay format and the means of detection in the reading zone etc. The detector reagent is "supported" in the conjugate zone in a manner such that when sample flows through the conjugate zone (ie. when the zone is wetted), the detector reagent is released and capable of being transported to the reading zone.

Various assays "formats" are possible according to assays procedures and techniques which are standard in the art, for example, sandwich, competition and inhibition-type assays. All such methods and detection means as are known in the art are covered, and the form of assay selected may dictate the choice of detector reagent. Generally, however, the detector reagent will be or will comprise one of a pair of affinity binding partners (ie. a ligand or an anti-ligand e.g. an antibody or an antigen/hapten).

In the case of a sandwich-type assay, the detector reagent will have a binding affinity for the analyte (ie. will be capable of binding to the analyte). In the case of a competition assay, the detector reagent will be capable of competing with the analyte for binding to a binding site (e.g. a binding partner). Thus, such a detector reagent will conveniently be or comprise the analyte or an analogue of the analyte (but will differ from the target analyte by being "detectable" ie. having a detectable moiety). Again, such "competitor molecules" are known in the art.

In the case of an inhibition assay, the detector reagent is such that its binding to a binding site (e.g. a binding partner) is inhibited by the presence of analyte. Thus, the detector reagent may have a binding affinity for the analyte.

The term "interacts with the target analyte" thus includes various forms of interaction, and encompasses detector reagents competing with the analyte as well as those having a binding affinity for it. Any form of interaction with the analyte, which permits the presence or amount of the target analyte variant to be determined is included in the scope of the invention.

The conjugate zone comprising the "detector reagent" is conveniently comprised of a material through which the sample may flow. The detector reagent is retained or held in the conjugate zone of the dipstick. The analyte passes through the conjugate zone. Sample flow to and through the conjugate zone conveniently releases the detector reagent. Thus, sample flow allows the detector reagent to be released and to flow through to the reading zone. The detector reagent may "interact" with the analyte in the conjugate zone or in the reading zone, or both. Thus, in the case of a detector reagent having a binding affinity for the analyte, the analyte binds to the detector reagent, to which, for example, a signal-producing substance is conjugated, and the analyte may thereby be labelled with the signal-producing substance. Suitable examples of signal-producing substances include, but are not limited to, coloured particles, colloids, dyes, enzymes, radioisotopes, chemoluminescent or fluorescent molecules. Particularly preferred signal producing substances in the dipstick of the present invention are particles, e.g. gold colloid particles and dyed latex particles such as blue-coloured latex particles. Such particles may readily be coated with, or may otherwise carry the binding ligand of the detector reagent. Other suitable signal-producing substances include tracers, markers and labels which are well known in the art and are often used in immunoassay technology by the skilled person. Any of the available such signal-producing substances could be used for any type of detector reagent according to the present invention.

A detector reagent having a binding affinity for the analyte may be any ligand capable of binding selectively to the analyte in general or to the target analyte in particular.

Thus, the detector reagent may be or may comprise an affinity binding partner for the analyte. Such a binding partner or ligand will conveniently and generally be a protein. Advantageously, the binding ligand may be antibody or an antibody fragment (e.g. as discussed above).

The dipstick assay of the invention is preferred for use in connection with the analysis of variants of transferrin e.g. CFT or asialotransferrin, and hence the binding ligand of the detector reagent (the "second binding ligand" of the dipstick) is preferably an anti-transferrin antibody, or a fragment thereof. The detector reagent may, as mentioned above, also be or comprise the analyte (by "analyte" here we mean either the analyte in general, or the target analyte variant in particular) or a fragment or portion or analogue thereof. The analogue may be a molecule or substance, for example, capable of competing with the analyte for binding to a binding partner. The analogue may thus be a derivative of the analyte or analyte variant, or a molecule having a spatial configuration etc. similar to the analyte target or analyte variant. In the case of determination of variants of transferrin, the detector reagent may thus be a transferrin molecule or a fragment thereof. In the case of such a "competitor" detector reagent, it may likewise be conjugated or coupled to a signal-producing substance e.g. particles.

The reading zone for detection of said analyte may be separate from the conjugate zone or may be part of it. The reading zone should be suitable at least for detection of the presence of the analyte, or it may be more sophisticated to allow the amount of analyte in the sample to be quantified. Various methods are known in the art for quantification of the analyte, for example a series of pads may be used in succession on the dipstick to show the amount of analyte present according to the colour of each pad and the number of pads which become coloured. The reading zone preferably comprises a solid support (e.g. a membrane, preferably a nitrocellulose membrane) having a capture reagent immobilised thereon. The capture reagent serves to "capture" the detector reagent and "fix" it on a solid surface or in immobilised form, to enable the detector reagent to be detected and the assay "read" in the reading zone. This capture may be direct or indirect. Thus, a detector reagent bound to the analyte may be captured by binding of the capture reagent to the bound analyte. Alternatively, the detector reagent may bind directly to the capture reagent.

The choice of capture reagent depends upon the detector reagent which is used, and/or on the type of assay format. In a sandwich-type assay, the capture reagent binds specifically only to the analyte (and not to the detector reagent). The detector reagent is thus bound only indirectly, by virtue of its being bound to the analyte.

In a competition-type of assay, the capture reagent is capable of binding both to the analyte and the detector reagent, whereby both detector reagent and analyte would compete for a limited number of binding sites on the capture reagent.

In an inhibition-type of assay, the capture reagent is specific for only the detector reagent (and does not bind directly to the analyte).

In any case, the capture reagent is a binding ligand (or binding partner) for either the analyte, or the detector reagent, or both.

In a preferred embodiment, the detector reagent preferably comprises a second binding ligand having a binding affinity for the analyte, and preferably a signal-producing substance is conjugated thereto. Advantageously, the reading zone also comprises as a capture reagent a third ligand having binding affinity for the analyte, and when the analyte reaches the reading zone it may or may not be labelled by means of the second ligand conjugated to the signal-producing substance. Thus, in this embodiment, the assay is of a sandwich-type.

Typically, both the second ligand from the conjugate zone and the third ligand from the reading zone will be antianalyte (e.g. anti-transferrin) antibodies, although any other suitable antibody or other ligand having binding affinity for the analyte could equally well be used. Where antibodies are used, however, pairs of analyte-binding antibodies having binding affinity for different epitopes of the analyte are suitable. These antibodies may be polyclonal or monoclonal in origin, and immunoreactive fragments of antibodies may also be used, as may other kinds of binding ligands which are specific for the analyte e.g. transferring.

In an inhibition-type of assay, the detector reagent will be capable of binding the analyte, and hence may be the same type of reagent as for the sandwich assay discussed above. In this case, however, the third ligand in the reading zone (ie. the capture reagent) will be capable of binding to the detector reagent only, and not to the analyte.

Thus, in this case the capture reagent (third ligand) may be a protein, for example, capable of binding to antibodies or fragments thereof, e.g. a protein capable of binding to the Fc portion of antibodies e.g. protein A or protein G or domains or portions thereof, or indeed it may be an antibody capable of binding specifically to the detector reagent, e.g. an antibody which binds the detector reagent at a different site to the analyte.

In a competition-type of assay, the capture reagent may be as for the sandwich assay embodiment described above. The detector reagent may for example be transferrin or a transferrin analogue, conjugated to a signal-giving substance.

The choice of antibody (or other binding ligand) will be dictated by a number of factors, including the sensitivity required of the assay. In general, if a monoclonal antibody is chosen as both the second "conjugate zone" ligand and as the third "reading zone" ligand, good sensitivity of the test may be achieved. Preferably, the antibody has a good level of specificity for the analyte, (or the detector reagent, as appropriate) such that a low level of background binding occurs. On the other hand, polyclonal antibodies may be used, and if this is done, generally a monoclonal antibody in conjunction with this for the alternative ligand. Where a monoclonal antibody is used as the third "reading zone" ligand, generally sensitivity may be poorer, high background levels of non-specific binding may occur and it may be necessary to treat the polyclonal antibodies by affinity purification techniques. Where a monoclonal antibody is used as the second "conjugate zone" ligand, a better degree of sensitivity may generally be achieved, e.g. moderate sensitivity, but there may still be the disadvantage of high background levels of non-specific binding and the need to treat the polyclonal antibodies by affinity purification techniques.

As mentioned above, the detector reagent has, or is provided with, a detectable moiety, conveniently a signal-producing moiety. This may be any signal-producing substance known in the art.

Preferably however, the signal-producing substance will be of a nature which allows it to be readily visualised for detection and/or quantitation purposes. Some labels will require the addition of other reagents in order to be visualised, and others may require the use of a particular instrument for this purpose. For example, where the signal-producing substance is an enzyme, the addition of a substrate reagent would be necessary, and fluorescent molecules may be detected by means of standard excitation/radiation techniques which are well-known in the art. Where reflectometers are used to detect electromagnetic radiation or where scanners are used to detect radioisotopes, instrumentation will be required to achieve this. On the other hand, coloured substances may be detected and visualised directly by the person carrying out the assay. Thus, any such method of visualisation and any signal-producing substance which avoids the need for the use of further equipment or the use of further reagents other than those contained in the dipstick are preferred.

Particulate labels which are directly visible (e.g. to the naked eye) are especially preferred. These may take the form of solid particles, which e.g. may be directly coloured or as vesicles which contain a visible substance e.g. a dye or other coloured substance. Such vesicles may e.g. by liposomes or similar vesicles, erythrocyte ghosts, polymer microcapsules etc. Other particles include polymeric nuclei coated with a signal-giving substance, or particles of an aqueous dispersion of a hydrophobic dye or pigment.

The visible particulate label may also be visible polymer particles, such as coloured polystyrene particles, e.g. of spherical shape.

As representative examples of other particulate labels by which the detector reagent would be visible, there may be mentioned: ferritin, phycoerythrins or other phycobiliproteins; precipitated or insoluble metals or alloys; fungal, algal, or bacterial pigments materials or derivatives, and the like.

A binding ligand (or analyte, or analyte analogue etc) may be labelled with the particulate label so as to produce a detector reagent for use in the invention by procedures generally known in the art, with the procedure which is used being dependent upon the binding ligand etc. and the particulate label which is employed. Such techniques include adsorption, covalent coupling, derivatisation or activation, and the like.

The conjugate zone conveniently is in the form of a conjugate pad, and this advantageously fulfills a number of different functions. Thus, the conjugate pad is preferably capable of taking up and holding a consistent of volume of detector reagent solution, and transferring the sample volume efficiently and consistently to the reading zone e.g. to the reading zone membrane. The conjugate zone is preferably also able to maintain the stability of the detector reagent. By this we mean that the detector reagent should be stable if stored as a dessicated solid for at least one year, preferably at least 18 months, and more preferably 2 years, 3 years or greater than 5 years. Preferably also the conjugate pad is able to release detector reagent consistently and quantitatively. The conjugate pad is preferably made from glass fibre filters, cellulosics (paper) or nonwoven filters, which have the properties as explained above with regard preferred materials for the sample pads. Unlike the sample pads however, woven fibre material is less preferred for the conjugate pads.

The detector reagent may be held or retained in the conjugate pad by any convenient means e.g. adsorption etc. and this is standard in dipstick technology.

A further function of the conjugate pad may be to control the volume of sample that is analyzed. Only the volume of sample that migrates before or with the detector reagent can contribute to the signal. Thus the sensitivity of the assay may be regulated by the characteristics of the conjugate pad. For example, lower sensitivity of the assay may occur when substantially all the conjugate is released after 5 microlitres of sample passes through the conjugate zone. Higher sensitivity of the assay may occur for example when 25 microlitres of sample is required before all the conjugate is released. Alternatively, variable sensitivity of the assay may be achieved if the conjugate is sometimes released after 5 microlitres of sample are passed through the conjugate zone, and sometimes when 25 microlitres of sample of sample pass therethrough. It will be appreciated however that the volumes of 5 and 25 microlitres quoted in these examples are illustrative of the principles of sensitivity of the assay, and are not limited thereto. Larger and smaller volumes of sample may achieve the same effect according to the capacity of the dipstick, which depends on a number of factors including the number of conjugate pads which are used and the capacity of each conjugate pad, as well as the amount of detector reagent contained in the conjugate pad.

Signal amplification systems may be used in connection with the detector reagent/detection means of the present invention, according to principles well known in the art. Thus for example, in the case of a detector reagent comprising a particulate label as signal-producing moiety, the amplification system may comprise a secondary particle having a binding affinity for the particulate label of the detector reagent (ie. the "first particle"). Thus the amplification reagent may be a particle (e.g. a particulate label as discussed above) conjugated to a binding ligand for e.g. an antigen or epitope on the first particle. The first particle may have a number of binding sites for the amplification reagent, and hence binding of a single first particle in the reading zone may lead to the binding of a plurality of secondary particles, and hence signal amplification may be achieved.

Other signal amplification systems may be used, as indeed may other detection means. For example enzyme or antibody conjugates combined with an enzyme substrate may be used in a similar manner. Chemiluminescent substrates, for example, are useful in this manner and are susceptible to signal amplification. Such systems may be useful in the context of low concentration analytes.

In general, sample volumes and detection technology in the conjugate and/or reading zones can be selected depending upon the selected reading modalities and the concentration of the target analyte variant to be detected. Combinations of different modalities may be used in the same dipstick, allowing for a two- or multi-step sensitivity device.

The conjugate pad may contain other reagents as well as the detector reagent, and this may present a number of advantages. For example, the conjugate pad may, in addition to the detector reagent, contain other reagents which are capable of preventing non-specific binding of the detector reagent and/or analyte. This would obviate or reduce the need to treat the reading zone with blocking agents to prevent non-specific binding in the reading zone. However, this possibility is also encompassed. Thus blocking agents can be pre-loaded into the conjugate pad, such that they are released with the detector reagent and flow into the reading zone. Examples of blocking agents include albumin, casein and gammaglobulin. Other standard blocking agents known in the art may also be used. Preferably, bovine serum albumin (BSA) is used. Other suitable blocking agents include a long list of proteins and polyvinyl alcohol, SDS and other materials known in the art. If it is desired that the blocking agent should contain no undesirable moieties such as carbohydrates or sialic acid residues, then these may be removed from the blocking agent using standard means e.g. enzymes.

In a preferred embodiment of the invention, the reading zone comprises a capture (test) zone and a control (negative) zone. The capture zone comprises a capture reagent immobilised thereon, and the capture reagent is preferably an antibody against the target analyte, as discussed above.

The capture reagent antibodies bind to the analyte-detector reagent complex such that the analyte-detector reagent complex may be detected in the capture zone. Thus, for example, the capture zone may comprise the capture reagent immobilised in a recognisable pattern, e.g. a strip oriented transverse to the direction of flow of the sample, to form a detectable "positive line" as the sample migrates past the capture zone.

The control zone comprises an immobilised reagent also bound to the membrane in a recognisable pattern, which captures the detector reagent and gives a detectable signal, such as the formation of a coloured line, if the test has been used properly. The control zone will give an identifiable signal whether or not there is an identifiable positive line, i.e. the control zone develops a detectable signal if the test has been used properly, regardless of whether any analyte was present in the sample being analysed.

Where a colorimetric detection means is used, i.e. where the detector reagent is conjugated to a signal-producing substance and the signal-producing substance is visible, such as a dyed latex particle, the intensity of colour which develops on the positive line is generally proportional to the concentration of analyte in the sample.

In general, in practice, the negative control line is formed due to any of the unbound detector reagent which is washed past the capture zone by the sample volume entering the conjugate pad after the detector reagent has been released.

A further optional feature of the dipstick of the invention is an absorbent pad which is conveniently placed at the end of the dipstick, preferably beyond the reading zone at the opposite end to the sample application zone. The absorbent pad is designed to absorb the sample after it has passed through the capture zone, and the capacity of the absorbent pad preferably determines the volume of sample tested.

Preferably, the dipstick may comprise a plastic backing to which one or all of the conjugate pad, reading zone (e.g. membrane) and absorbent pad are attached directly or indirectly, for example by means of an adhesive. The membrane is preferably made of nitrocellulose. The sample application zone and/or screening zone (e.g. sample and/or screening pads) may also be attached directly or indirectly to the plastic backing.

In a particularly preferred embodiment of the invention, the analyte is quantified by means of the label-detection means, and thus the quantity of analyte arriving at the reading zone and remaining immobilised in the reading zone is proportional to the amount of analyte in the sample.

Alternatively however, in an embodiment which is less preferred, the total amount of analyte e.g. transferrin (ie. all analyte variants) in the initial sample may be measured, and the amount of analyte which is not retained in the "screening zone" may then be calculated by measuring the amount of analyte (e.g. transferrin) which is not retained by the first binding ligand in the screening zone i.e. the amount of analyte (e.g. transferrin) which is labelled and subsequently immobilised in the reading zone.

In general, besides the sample under evaluation, calibration samples with known analyte contents will also be assessed in the performance of the assay method of the invention. Such determinations can be used to plot a calibration curve from which the CFT content of the sample under evaluation may be determined. In the case of transferrin, preferably calibration samples having transferrin contents of up to 0.05 mg/mL (e.g. 0.002, 0.01, 0.02 and 0.03 mg/ml) will be used. (These will not of course be passed through the carbohydrate-binding ligands to separate out the carbohydrate-containing variants).

Moreover in the assay method of the invention the total transferrin content of the sample may preferably be determined, using any convenient assay procedure (e.g. turbidimetry etc). However, preferably, the same assay procedure i.e. dipstick assay e.g. an immuno-chromatography test stip for "total" transferrin (ie. all transferrin variants). In this way the CFT content may be determined as a percentage of total transferrin (%CFT). %CFT may be a more precise marker for alcohol consumption than total CFT, and a threshold value, for example 1%, may be set. From a diagnostic point of view however, it may reasonably be assumed that the presence of any CFT whatsoever is indicative of alcohol abuse.

Alternatively, the CFT may be assessed as an actual concentration (ie. a mass per unit volume).

A reading to quantify the analyte may be performed for example by the use of dedicated reflectometers, or alternatively a flat-bed PC scanner of the type described in WO 98/32004 may be used.

Calibration may be carried out either by the use of a calibration sample having a known analyte (e.g. asialotransferrin) content, measured by independent reference methods such as the method disclosed in Alcoholism: Clinical and Experimental Research Vol 21 No. 9 p1710–1715, 1997, "Transferrin isoform distribution: Gender and Alcohol Consumption" of Martensson et al. In this paper, the use of HPLC isolation, followed by radioimmunoassay quantitation of the transferrin content in each isolated fraction, allows the content of asialotransferrin to be measured in mg asialo transferrin per liter or as a percentage of total transferrin content.

In its most general sense, the dipstick assay of the invention involves simply contacting the sample with the binding ligand(s) (for screening) and measuring or detecting the separated fraction which does not bind. Preferably the binding ligand is a carbohydrate-binding ligand.

Thus viewed from a different aspect, the invention provides a dipstick for determining the content of an analyte variant (a "target analyte variant") in a mixture of analyte variants in a sample, comprising:

a) a zone for contacting a sample with a binding ligand having a binding affinity for a variant of said analyte which is (are) not to be determined (ie. non-target analyte variants), to allow separation of a non-binding fraction containing the analyte variant to be determined;

b) a zone for determining the analyte content of the non-binding fraction.

In a preferred embodiment this aspect of the invention provides a dipstick comprising:

a) a zone for contacting a sample and a carbohydrate-binding ligand to allow separation of a non-binding fraction containing the analyte to be detected, b) a zone for determining the analyte content of the non-binding fraction.

Preferably, the carbohydrate-binding ligand is a lectin or mixture thereof and the analyte to be detected is CFT. The non-binding fraction under these circumstances may thus be regarded as substantially free of carbohydrate. Alternatively, as mentioned above, the non-binding fraction may also comprise CDT variants (in particular mono- and/or disialo-transferrins) in addition to the CFT.

Thus, according to the preferred aspect, the present invention also provides a method for the determination of carbohydrate-free transferrin in a body fluid for use in the assessment of alcohol consumption, said method comprising (a) contacting a sample of said body fluid with a carbohydrate-binding ligand, to bind carbohydrate or carbohydrate-containing moieties in said sample to said ligand;

(b) separating a fraction not binding to said ligand and (c) determining the content of transferrin in said fraction, wherein said carbohydrate-binding ligand is immobilised on a dipstick and wherein said separation and determination steps (b) and (c) take place on said dipstick.

By "substantially free of carbohydrate" is meant that the molecules contained in this fraction are substantially carbohydrate-free (ie. at least 60% of the molecules are free of carbohydrate, eg. at least 70, 80, 90 or 95% being free of carbohydrate).

In this regard, it will be understood by the skilled reader that the nature of scientific and analytical laboratory procedures and biological material is such that absolute precision and uniformity of behaviour can never be guaranteed and that 100% separation may not always be achieved. In any such system some tolerance must be allowed for and this is a principle accepted in the art. In the separation system of the present invention clinical utility may be preserved even though separation may not be 100% complete.

In particular, it has been found that where the analyte is transferrin, variants of transferrin with a low carbohydrate content (i.e. the CDT variants mono- and disialo-transferrin) may bind to the carbohydrate-binding ligands with a low affinity, in particular with a lower affinity than the transferrin variants with a higher or high carbohydrate content (i.e. the higher sialylated transferrins penta-tetra- and tri-sialo transferrins), and hence may not all be retained in the "binding" fraction. Thus, in carrying out the separation step according to the invention (i.e. in the screening zone), carbohydrate-carrying variants of CDT (i.e. the lower sialylated variants) may be separated with lower efficiency, and hence may also be separated into the "non-binding" fraction, along with CFT. In particular, it has been found that a portion or fraction of the disialo- and/or monosialo-transferrin content of the sample may be separated into the "non-binding" fraction, along with CFT (asialo-transferrin). In other words an incomplete separation of CFT may be achieved, in which the separated ("non-binding") fraction may contain CFT and some or all of the monosialo-transferrin and some disialo-transferrin. As noted above, the invention can tolerate this incomplete separation of CFT without compromising the clinical value of the assay.

In particular, the separation achievable in a given system has been found to be reproducible, and hence, since for a given separation procedure, the type and amount or proportion of the variants separated will be constant (i.e. reproducible), this incomplete separation can be accounted for—the actual amounts or proportion of the different variants separated do not matter, as long as the separation is reproducible between runs. Furthermore, it has surprisingly been found that there is a high correlation between asialo- (CFT) and disialo-transferrin contents in a sample and since disialotransferrin is also a strong marker for alcoholism, this disialo-fraction can be taken into account in determination. In other words, calculations can be performed taking into the amounts, values, or concentrations determined for the mono- and disialo-content of the sample. This can be done using mathematical techniques and correlation standard in the art.

All the methods and assays of the prior art, including those which are currently being exploited commercially, are based on the identification and quantitation of different transferrin variants on the basis of differences in charge and hence pI of the different variants. Where the primary structure ie. the amino-acid sequence of transferrin variants is constant, these differences in charge arise due to the loss of negatively charged sialic acid residues, which increases the pI of the transferrin variants incrementally with each sialic acid residue lost.

However, the primary structure of the transferrin polypeptide is known to be polymorphic and the prevalence of particular amino-acid sequence isoforms differs according to racial origin. For example, relative to "normal" transferrin which predominates in Caucasian populations, the transferrin D variant possesses a single, non-conservative amino-acid substitution in the polypeptide backbone which affects the isoelectric point of the transferrin variant. The D variant is common within populations of Japanese and black African origin. The non-conservative amino-acid substitution changes the net charge and hence pI of the transferrin backbone with the result that in iso-electric focussing or equivalent studies, many false positive results are generated in relation to persons of Japanese or black African origin. Clearly this is unacceptable, and means that in populations where the transferrin D variant is common, a second test must be carried out to establish which transferrin variant is expressed by the individual under study. This adds greatly to the overall cost, time taken and complexity of the assessment of alcoholism.

Since in its preferred embodiment where the analyte is CFT (or CFT plus variants of CDT), the assay of the present invention relies solely on the presence or absence of carbohydrate moieties associated with the polypeptide backbone of transferrin, it is not influenced by polymorphisms in the amino acid sequence, and therefore it is not subject to any false positives or negatives on account of the variant polymorphism expressed by the individual under clinical evaluation. Hence, the present invention is particularly advantageous in that it is racially independent.

The invention will now be illustrated by the following non-limiting Examples and the accompanying figures in which:

FIG. 1 shows a dipstick according to a preferred embodiment of the invention. Particles coated with lectin are shown on the sample pad (2); particles coated with anti-transferrin are shown on the conjugate pad (4); capture reagents (anti-transferrin antibodies) are shown on the test line (6) and capture reagents (secondary antibodies) are shown on the control line 7).

The dipstick is made of a dry hydrophilic wicking material such as nitrocellulose which provides a support comprising a binding and adhesive (1) for the different pads and immobilised zones contained on it. The sample to be tested is applied to the sample application zone (sample pad (2)), and is drawn through the dipstick by natural diffusion and with the aid of the adsorbent sink pad (3) which is provided on the opposite end of the dipstick. Immobilised lectins are provided on the first part of the dipstick either on a separate pad which is in contact with the sample application pad, or on the sample pad itself (as shown in the drawing). The conjugate release pad (4) is also in contact with the immobilised lectin zone so that the zones are in free-flow communication with each other and the sample flows through each zone in turn e.g. via the membrane (5). The conjugate release pad (4) contains the labelled detector reagent, for example consisting of an anti-transferrin antibody conjugated to a blue latex particle label. The reading zone which comprises a test line (6) and the control reading zone which may comprise a control line (7) are in contact with the conjugate release zone (4) but spaced a distance therefrom, and on these the antibodies are immobilised in a stripe across the dipstick such that a coloured blue stripe is seen when the asialotransferrin-labelled molecules are bound to the antibodies. The depth of colour seen on the dipstick indicates the quantity of asialotransferrin contained in the sample and allows a diagnosis of alcoholism to be made where a positive result is obtained.

Example 1 shows the results using a dipstick according to a particularly preferred embodiment of the invention.

EXAMPLE 1

Quantitation of CFT by Means of Immobilised Lectin From *Sambuccus Nigra* in a Dipstick Format a. A 10 µl serum sample was mixed with 0.5 ml 20 mM TRIS buffer pH=7.5 comprising 150 mM sodium chloride.

b. A dipstick was inserted into the mixture such that the sample contacts the sample application area of the dipstick and the mixture was allowed to wick through the dipstick device. The dipstick used consisted of a sample application zone comprising a single pad made of glass fibre material and this was in direct contact with a second pad (the screening zone) also made of glass fibre material with a mixture of SNA lectin and ConA immobilised on it. The dipstick has a conjugate release zone in contact with the lectin-containing "screening zone", and the detector reagent was an anti-transferrin antibody labelled with a blue latex particle. After the conjugate release zone the dipstick contains a reading zone which contains anti-transferrin antibodies immobilised on it on the nitrocellulose membrane support material of the dipstick. The immobilised anti-transferrin antibodies were additionally coated with blocking agent (BSA) to hinder non-specific protein adsorption. Finally, an adsorbent sink pad is provided on the far end of the dipstick (i.e. the opposite end to the sample application zone) and this "pulls" the sample through the dipstick such that it contacts each of the different "zones" of the dipstick in turn and within a reasonable time-frame.

c. The colour intensity of the inspection area was measured by reflectometry, and the asialotransferrin content of the sample was calculated from this.

What is claimed is:

1. A dipstick for determining the content of a target analyte variant in a mixture of analyte variants in a sample, comprising:
   (a) a zone for contacting a sample with a binding ligand having a binding affinity for a non-target analyte variant, to allow separation of a non-binding fraction containing the target analyte variant;
   (b) a zone for determining the analyte content of the non-binding fraction, wherein said target analyte variant is a carbohydrate-free variant of said analyte,
      and wherein said carbohydrate free variant is carbohydrate-free transferrin (CFT) or asialotransferrin.

2. The dipstick as claimed in claim 1 wherein said target analyte variant comprises carbohydrate-free transferrin and disialotransferrin.

3. The dipstick as claimed in claim 1 wherein said target analyte variant comprises carbohydrate-free transferrin, monosialotransferrin and disialotransferrin.

4. The dipstick as claimed in claim 1 wherein said binding ligand having a binding affinity for a non-target analyte variant is capable of binding selectively to an oligosaccharide or sugar structure or carbohydrate-containing moieties on said non-target variant.

5. The dipstick as claimed in claim 4 wherein said binding ligand having a binding affinity for a non-target analyte variant is a sialic-acid binding lectin.

6. The dipstick as claimed in claim 1 wherein said binding ligand having a binding affinity for a non-target analyte variant is a carbohydrate-binding lectin or a mixture thereof, and the target analyte variant is carbohydrate-free transferrin (CFT).

7. The method for the determination of carbohydrate-free transferring in a body fluid for use in the assessment of alcohol consumption, said method comprising
  (a) contacting a sample of said body fluid with a carbohydrate-binding ligand, to bind carbohydrate or carbohydrate-containing moieties in said sample to said ligand;
  (b) separating a fraction not binding to said ligand and
  (c) determining the content of transferring in said fraction, wherein said carbohydrate-binding ligand is immobilised on a dipstick as claimed in claim 1 and wherein said separation and determination steps (b) and (c) take place on said dipstick.

8. The method of determining the content of a target analyte variant in a mixture of analyte variants in a sample comprising:
  contacting said sample with a dipstick as claimed in claim 1 and
  determining the content of said target analyte variant in said sample,
  wherein said target analyte variant is a carbohydrate-free variant of said analyte.

9. The method as claimed in claim 8 wherein said target analyte variant comprises carbohydrate-free transferrin monosialotransferrin and disialotransferrin.

10. The method as claimed in claim 8 wherein said sample comprises a body fluid.

11. The method as claimed in claim 10 wherein said body fluid is urine or blood or a blood-derived sample.

12. The method as claimed in claim 8 wherein said target analyte variant comprises carbohydrate-free transferrin and disialotransferrin.

13. The method as claimed in claim 7 wherein said determining step comprises quantifying the carbohydrate-free transferrin or carbohydrate-free target analyte variant.

14. A dipstick for determining the content of a target analyte variant in a mixture of analyte variants in a sample, comprising:
  (i) a sample application zone,
  (ii) A screening zone having an immobilized binding ligand having a binding affinity for a non-target analyte variant or variants,
  (iii) a conjugate zone comprising a detector reagent, wherein said detector reagent comprises a second ligand having a binding affinity for the analyte and said second ligand is an anti-transferrin antibody or a fragment thereof,
  (iv) a reading zone for detection of said analyte,
    wherein said target analyte variant is a carbohydrate-free variant of said analyte which is a carbohydrate-free transferrin (CFT) or asialotransferrin.

* * * * *